(12) United States Patent
Bozzano et al.

(10) Patent No.: US 8,680,348 B2
(45) Date of Patent: Mar. 25, 2014

(54) METHODS FOR PRODUCING LINEAR ALKYLBENZENES, PARAFFINS, AND OLEFINS FROM NATURAL OILS AND KEROSENE

(71) Applicant: UOP LLC, Des Plaines, IL (US)

(72) Inventors: Andrea G. Bozzano, Northbrook, IL (US); Stephen W. Sohn, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/855,065

(22) Filed: Apr. 2, 2013

(65) Prior Publication Data

US 2013/0253241 A1    Sep. 26, 2013

Related U.S. Application Data

(62) Division of application No. 13/427,718, filed on Mar. 22, 2012, now Pat. No. 8,502,005.

(51) Int. Cl.
*C07C 1/24* (2006.01)
*C07C 1/20* (2006.01)

(52) U.S. Cl.
USPC .......................................... 585/240; 585/733

(58) Field of Classification Search
USPC .................................................. 585/733, 240
See application file for complete search history.

(56) References Cited

U.S. PATENT DOCUMENTS

2009/0158637 A1*    6/2009    McCall et al. .................. 44/308

* cited by examiner

*Primary Examiner* — Thuan D Dang
(74) *Attorney, Agent, or Firm* — Maryann Maas (57) ABSTRACT

A method for producing a linear paraffin product from natural oil and kerosene includes providing a first feed stream comprising kerosene, pre-fractionating the first feed stream to produce a heart cut paraffin stream comprising paraffins in a heart cut range, and combining the heart cut paraffin stream with a second feed stream comprising natural oil to form a combined stream. The method further includes deoxygenating the natural oil and fractionating the combined stream to remove paraffins that are heavier than the heart cut range.

3 Claims, 5 Drawing Sheets

METHODS FOR PRODUCING LINEAR ALKYLBENZENES, PARAFFINS, AND OLEFINS FROM NATURAL OILS AND KEROSENE

CROSS REFERENCE TO RELATED APPLICATION

This application is a Division of copending application Ser. No. 13/427,718 filed Mar. 22, 2012, the contents of which are hereby incorporated by reference in its entirety.

FIELD OF THE INVENTION

The present invention relates generally to methods for producing renewable detergent compounds, and more particularly relates to methods for producing linear alkylbenzenes, paraffins, and olefins from natural oils and kerosene.

BACKGROUND OF THE INVENTION

While detergents made utilizing linear alkylbenzene-, paraffin-, and olefin-based surfactants are biodegradable, processes for creating linear alkylbenzenes, paraffins, and olefins are not based on renewable sources. Specifically, linear alkylbenzenes, paraffins, and olefins are traditionally produced from kerosene extracted from the earth. Due to the growing environmental concerns over fossil fuel extraction and economic concerns over exhausting fossil fuel deposits, there is a demand for incorporating alternate feed sources with the traditional kerosene feed source for producing biodegradable surfactants for use in detergents and in other industries.

Accordingly, it is desirable to provide methods for producing linear alkylbenzenes, paraffins, and olefins from a feed source that includes natural oils, i.e., oils that are not extracted from the earth, in addition to kerosene. Furthermore, other desirable features and characteristics of the present invention will become apparent from the subsequent detailed description of the invention and the appended claims, when taken in conjunction with the accompanying drawing and this background of the invention.

SUMMARY OF THE INVENTION

Methods for producing a linear alkylbenzene, paraffin, or olefin product from a natural oil and kerosene feed source are provided herein. In accordance with an exemplary embodiment, a method for producing a linear paraffin product from natural oil and kerosene includes providing a first feed stream comprising kerosene, pre-fractionating the first feed stream to produce a heart cut paraffin stream comprising paraffins in a heart cut range, and combining the heart cut paraffin stream with a second feed stream comprising natural oil to form a combined stream. The method further includes deoxygenating the natural oil and fractionating the combined stream to remove paraffins that are heavier than the heart cut range.

In another exemplary embodiment, a method for producing a linear olefin product from natural oil and kerosene includes providing a first feed stream comprising kerosene, pre-fractionating the first feed stream to produce a first heart cut paraffin stream comprising paraffins in a heart cut range, and combining the first heart cut paraffin stream with a second feed stream comprising natural oil to form a combined stream. The method further includes deoxygenating the natural oil, fractionating the combined stream and removing paraffins that are heavier than the heart cut range to form a second heart cut paraffin stream, and dehydrogenating the second heart cut paraffin stream to form a stream comprising olefins.

In accordance with yet another exemplary embodiment, a method for producing a linear alkylbenzene product from natural oil and kerosene includes providing a first feed stream comprising kerosene, pre-fractionating the first feed stream to produce a first heart cut paraffin stream comprising paraffins in a heart cut range, and combining the first heart cut paraffin stream with a second feed stream comprising natural oil to form a combined stream. The method further includes deoxygenating the natural oil, fractionating the combined stream and removing paraffins that are heavier than the heart cut range to form a second heart cut paraffin stream, dehydrogenating the second heart cut paraffin stream to form a stream comprising olefins, and alkylating the stream comprising olefins with a third feed stream comprising benzene to form a stream comprising alkylbenzenes.

BRIEF DESCRIPTION OF THE DRAWINGS

Embodiments of the present invention will hereinafter be described in conjunction with the following drawing figures, wherein.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Various embodiments contemplated herein relate to methods for producing a linear alkylbenzene, paraffin, or olefin product from natural oils and kerosene. It will be appreciated that embodiments of the present disclosure allow for increased use of the $C_{10}$ content in the kerosene feed. As will be appreciated by those having ordinary skill in the art, only a certain percentage of $C_{10}$ (generally about 10% to about 15%) is allowed to be included in a linear alkylbenzene product for use in detergents. Traditionally, where only kerosene was used as a feed stock, any $C_{10}$ present in an amount beyond this maximum needed to be removed from the system and discarded or put to use for the production of other products. By supplementing the feed with a natural oil source, which generally has a higher content of heavier hydrocarbons, the producer can increase the use of $C_{10}$ from the kerosene feed while still maintaining the same 10%-15% content. Table 1, presented below, shows an exemplary illustration of the benefits realized by supplementing a kerosene feed with natural oils. Table 1 is provided merely for illustration, and is not limiting on the possible benefits, $C_\#$-compositions, or natural oil/kerosene feed amounts realizable in accordance with the teachings of the present disclosure.

TABLE 1

|  | Example 1 | Example 2 | Feed 1/Feed 2 |
|---|---|---|---|
| Natural C12 | 34000 | 0 |  |
| Feed MTA | 242726 | 527933 | 0.46 |
| Extract MTA | 74000 | 74087 |  |
| Product Purity | 0.985 | 0.985 |  |
| Product Aromatics, | 0.005 | 0.005 |  |
| Product C# Distribution |  |  |  |
| nC9 | 0 | 0 |  |
| nC10 | 15.03 | 14.98 |  |
| nC11 | 15.11 | 32.82 |  |
| nC12 | 57.88 | 27.93 |  |
| nC13 | 10.29 | 22.35 |  |
| nC14 | 0.19 | 0.42 |  |
|  | 98.5 | 98.5 |  |
| AMW Target range | 164.4 | 163.4 |  |

As shown in Table 1, in Example 1, 34,000 kg of natural oil are provided with 242,726 MTA feed (kerosene). The $C_{10}$ percentage in the product is about 15%. In Example 2, however, a greater amount of feed MTA, 527,933 kg is required to achieve the same about 15% $C_{10}$ product where no natural oils were provided. As such, in Example 1, a reduction of 54% MTA feed is realized (MTA Feed 1/Feed 2=0.46, as shown in Table 1) by providing natural oils.

Figure 1:
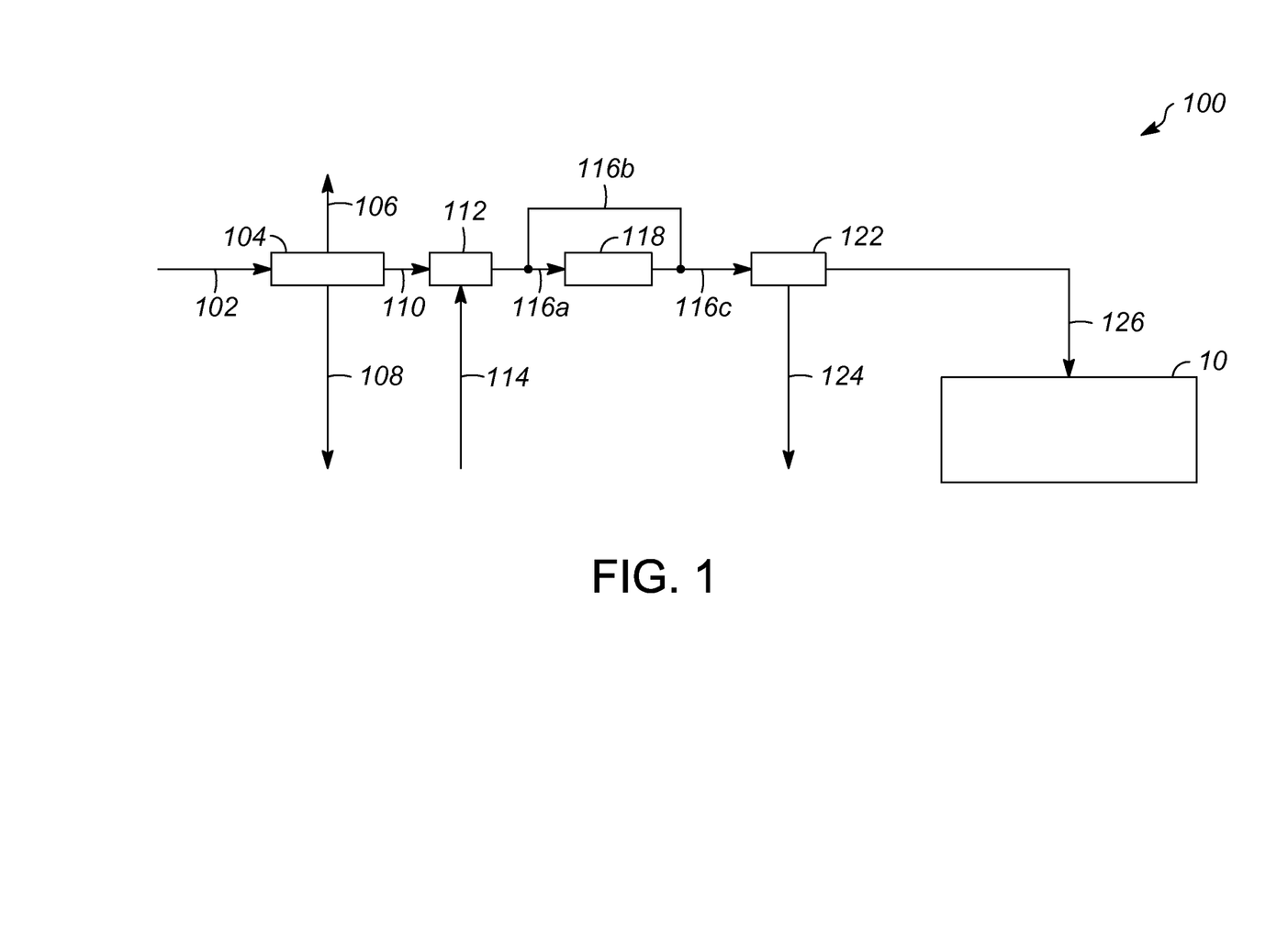
FIG. 1 schematically illustrates an exemplary embodiment of a system utilizing a process for producing linear alkylbenzenes, paraffins, and/or olefins from natural oils and kerosene.

In FIG. 1, an exemplary system 100 utilizing an exemplary process for producing a linear alkylbenzene, paraffin, and/or olefin product is depicted. A kerosene (also known as paraffin oil) feed 102 is fed into a pre-fractionator 104. The pre-fractionator 104 fractionates the kerosene feed 102 into three streams 106, 108, and 110. Stream 106 is a light hydrocarbon stream that includes, in one embodiment, $C_9$ hydrocarbons and lighter hydrocarbons (i.e., hydrocarbons having fewer carbons) that were separated from the kerosene feed 102. In other embodiments, stream 106 may include $C_8$ and lighter hydrocarbons or $C_{10}$ and lighter hydrocarbons, depending on the desired product composition of linear alkylbenzenes, paraffins, and olefins. Stream 108 is a distillate, or heavy hydrocarbon stream that includes, in one embodiment, $C_{14}$ and heavier hydrocarbons (i.e., hydrocarbons having more carbons) that were separated from the kerosene feed 102. In other embodiments, stream 108 may include anywhere from $C_{13}$-$C_{19}$ and heavier hydrocarbons, depending on the desired product composition of linear alkylbenzenes, paraffins, and olefins. Stream 110 includes hydrocarbons that are selected for further processing into the desired linear alkylbenzenes, paraffins, and olefins, and is referred to as the "heart cut." The heart cut stream 110, in one embodiment, includes $C_{10}$-$C_{13}$ hydrocarbons that were separated from the kerosene feed 102. In another embodiment, stream 110 includes $C_{10}$-$C_{18}$ hydrocarbons. Generally, the heart cut can include any range of hydrocarbons within the $C_9$-$C_{19}$ range. Light hydrocarbon stream 106 and distillate stream 108 are removed from the system 100 and may be used in other processes.

With continued reference to FIG. 1, in an exemplary embodiment, heart cut stream 110 continues within system 100 for further processing in a kero-hydrotreater (KHT) 112. KHT 112 is employed to treat the heart cut stream of hydrocarbons 110 to reduce the naturally occurring nitrogen and sulfur content in kerosene to acceptable levels for use in detergents. KHT 112 is a catalyst-based apparatus, and various catalysts for denitrification and desulfurization are known to those having ordinary skill in the art. In the embodiment depicted in FIG. 1, the KHT 112 also receives a feed stream of natural oil 114. As used herein, natural oils are those derived from plant or algae matter, and are often referred to as renewable oils. Natural oils are not based on kerosene or other fossil fuels. In certain embodiments, the natural oils include, but are not limited to, one or more of coconut oil, babassu oil, castor oil, algae 1 byproduct, beef tallow oil, borage oil, camelina oil, Canola® oil, choice white grease, coffee oil, corn oil, *Cuphea Viscosissima* oil, evening primrose oil, fish oil, hemp oil, hepar oil, jatropha oil, *Lesquerella Fendleri* oil, linseed oil, *Moringa Oleifera* oil, mustard oil, neem oil, palm oil, perilla seed oil, poultry fat, rice bran oil, soybean oil, stillingia oil, sunflower oil, tung oil, yellow grease, cooking oil, and other vegetable, nut, or seed oils. Other natural oils will be known to those having ordinary skill in the art. The natural oils typically include triglycerides, free fatty acids, or a combination of both, and other trace compounds.

In embodiments where, as in FIG. 1, the natural oil feed 114 and the kerosene heart cut 110 are combined in the KHT 112, the KHT is also configured to deoxygenate the natural oil feed 114 to produce paraffins. The triglycerides and fatty acids in the natural oil feed 114 are deoxygenated and converted into linear paraffins in the KHT 112, using a catalyst that is suitable for both deoxygenation and denitrification/desulfurization or a mix of catalysts that each accomplish one or more of deoxygenation, denitrification, and desulfurization. A suitable KHT 112 apparatus for use in embodiments of the present disclosure is sold by UOP LLC. Structurally, triglycerides are formed by three, typically different, fatty acid molecules that are bonded together with a glycerol bridge. The glycerol molecule includes three hydroxyl groups (HO—), and each fatty acid molecule has a carboxyl group (COOH). In triglycerides, the hydroxyl groups of the glycerol join the carboxyl groups of the fatty acids to form ester bonds. Therefore, during deoxygenation, the fatty acids are freed from the triglyceride structure and are converted into linear paraffins. The glycerol is converted into propane, and the oxygen in the hydroxyl and carboxyl groups is converted into either water or carbon dioxide. The deoxygenation reaction for fatty acids (1) and triglycerides (2) are illustrated, respectively, as:

During the deoxygenation reaction, the length of a product paraffin chain R″ will vary by a value of one depending on the exact reaction pathway. For example, if carbon dioxide is formed, then the chain will have one fewer carbon than the fatty acid source (R″). If water is formed, then the chain will match the length of the R″ chain in the fatty acid source. Typically, due to the reaction kinetics, water and carbon dioxide are formed in roughly equal amounts, such that equal amounts of $C_X$ paraffins and $C_{X-1}$ paraffins are formed.

In some embodiments, a treated stream of paraffins 116a exiting KHT 112 may be fed to a separator 118 to separate the desirable linear paraffins from branched or cyclic compounds that may be included in the stream 116a. A suitable separator for this purpose is a separator that operates using the UOP LLC Molex® process, which is a liquid-state separation of normal paraffins from branched and cyclic components using UOP LLC Sorbex® technology. Other separators known in the art are suitable for use herein as well. In other embodiments, depending on the composition of the kerosene feed 102 and/or the natural oil feed 114, separation of normal paraffins from branched and cyclic components is not necessary, and a treated stream of paraffins 116b from the KHT 112 may be directed downstream for further processing.

A linear paraffin stream 116c exiting the separator 118, or the treated stream of paraffins 116b, is fed to a fractionator 122. As discussed above, the pre-fractionator 104 removed light and heavy hydrocarbons from the kerosene feed 102; however, the natural oil feed 114 may include hydrocarbons that are heavier than the heart cut range, and as such the fractionator 122 is provided to fractionate hydrocarbons that are heavier than the desired heart cut range. In one embodiment, hydrocarbons that are $C_{14}$ and heavier are removed from system 100 in a heavy paraffins stream 124, and may be used in other processes, as in stream 108. In other embodiments, hydrocarbons anywhere in the range from $C_{15}$-$C_{18}$ and heavier are removed from system 100 in the heavy paraffins stream 124. The paraffins in the desired heart cut range exit the fractionator 122 in a stream 126 for further processing into linear alkylbenzene, paraffin, and/or olefin products in subsystem 10, as will be described in greater detail below.

Figure 2:
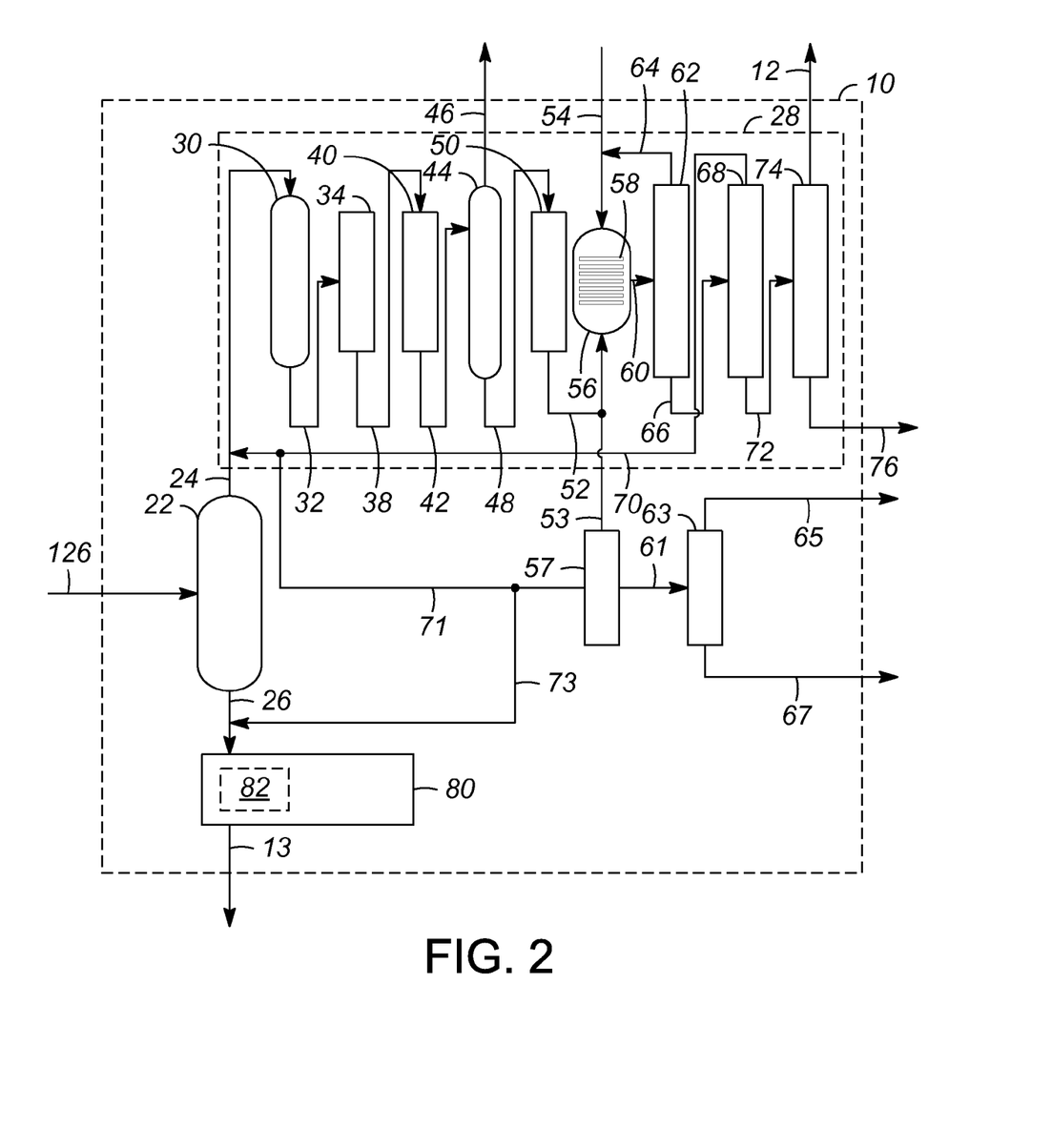
FIG. 2 illustrates an exemplary subsystem of the system shown in FIG. 1 for producing linear alkylbenzenes, paraffins, and/or olefins.

In FIG. 2, an exemplary subsystem 10 utilizing an exemplary process for producing a linear alkylbenzene, paraffin, or olefin product is depicted. Subsystem 10 receives as its feed stream the stream 126 from the fractionator 122 including the heart cut of linear paraffins. Stream 126 is fed to a separator 22. The separator 22 may be a multi-stage fractionation unit, distillation system, or similar known apparatus. In any event, the separator 22 provides a means to separate the paraffins into various desirable fractions, or into various portions for producing one or more of linear alkylbenzenes, paraffins, and olefins. For example, as shown in FIG. 2, a first portion of paraffins 24 and a second portion of paraffins 26 are illustrated, although any number of paraffin portions may be provided. Portion 24 may include the same hydrocarbon range as portion 26, or they may be separated into different fractions. For example, where the heart cut is selected as $C_{10}$-$C_{18}$, portion 24 may include $C_{10}$-$C_{13}$ paraffins, whereas portion 26 may include $C_{14}$-$C_{18}$ paraffins. Alternatively, they may both include $C_{10}$-$C_{18}$ paraffins. In another example, where the heart cut is selected as $C_{10}$-$C_{13}$, both portions 24 and 26 may include hydrocarbons in that range. Numerous other examples are possible, depending on the quantity and the hydrocarbon content of the desired product linear alkylbenzenes, paraffins, and/or olefins.

Either or both paraffin portions 24 or 26 (or other portions if more are present) may thereafter be purified to remove trace contaminants, resulting in a purified paraffin product. In some embodiments, wherein only paraffin production is desired, the entire paraffin product (i.e., all of the one or more portions) may be purified at this stage. In other embodiments, some of the paraffin product is directed to further processing stages for the production of alkylbenzenes and/or olefins. In still other embodiments, wherein only olefin and/or alkylbenzene production is desired, the entire paraffin product (i.e., all of the one or more portions) may be directed to further processing stages. As shown in the example embodiment illustrated in FIG. 2, the second paraffin portion 26 is directed to a purification system 80 to remove any remaining trace contaminants, such as oxygenates, nitrogen compounds, and sulfur compounds, among others, that were not previously removed in the processing steps described above. In one example, purification system 80 is an adsorption system. Alternatively or additionally, a PEP unit 82, available from UOP LLC, may be employed as part of purification system 80. Subsequent to purification, a purified paraffins stream 13 is removed from the system 10 as the paraffin product.

As further shown in FIG. 2, the first portion of paraffins 24 (i.e., that portion of linear paraffins directed for further processing to linear alkylbenzenes and/or olefins, where desired) is introduced to a linear alkylbenzene and olefin production zone 28. Specifically, the first portion of paraffins 24 is fed into a dehydrogenation unit 30 in the linear alkylbenzene and olefin production zone 28. In the dehydrogenation unit 30, the first portion of paraffins 24 is dehydrogenated into mono-olefins of the same carbon numbers as the first portion of paraffins 24. Typically, dehydrogenation occurs through known catalytic processes, such as the commercially popular Pacol process. Conversion is typically less than about 30%, for example less than about 20%, leaving greater than about 70% paraffins unconverted to olefins. Di-olefins (i.e., dienes) and aromatics are also produced as an undesired result of the dehydrogenation reactions as expressed in the following equations:

Mono-olefin formation: $C_XH_{2X+2} \rightarrow C_XH_{2X} + H_2$

Di-olefin formation: $C_XH_{2X} \rightarrow C_XH_{2X-2} + H_2$

Aromatic formation: $C_XH_{2X-2} \rightarrow C_XH_{2X-6} + 2H_2$

In FIG. 2, a dehydrogenated stream 32 exits the dehydrogenation unit 30 comprising mono-olefins and hydrogen, unconverted paraffins, as well as some byproduct di-olefins and aromatics. The dehydrogenated stream 32 is delivered to a phase separator 34 for removing the hydrogen from the dehydrogenated stream 32. The removed hydrogen can be directed away from system 100, or it can be used as fuel or as a source of hydrogen ($H_2$) for a deoxygenation process.

At the phase separator 34, a liquid stream 38 is formed and includes the mono-olefins, the unconverted paraffins, and any di-olefins and aromatics formed during dehydrogenation. The liquid stream 38 exits the phase separator 34 and enters a selective hydrogenation unit 40. In one exemplary embodiment, the hydrogenation unit 40 is a DeFine® reactor (or a reactor employing a DeFine® process), available from UOP LLC. The hydrogenation unit 40 selectively hydrogenates at least a portion of the di-olefins in the liquid stream 38 to form additional mono-olefins. As a result, an enhanced stream 42 is formed with an increased mono-olefin concentration.

As shown, the enhanced stream 42 passes from the hydrogenation unit 40 to a light hydrocarbons separator 44, such as a stripper column, which removes a light end stream 46 containing any light hydrocarbons, such as butane, propane, ethane and methane, that resulted from cracking or other reactions during upstream processing. With the light hydrocarbons 46 removed, stream 48 is formed and may be delivered to an aromatic removal apparatus 50, such as a PEP unit available from UOP LLC. As indicated by its name, the aromatic removal apparatus 50 removes aromatics from the stream 48 and forms a stream of mono-olefins and unconverted paraffins 52.

In FIG. 2, to produce linear alkylbenzenes, the stream of mono-olefins 52 and a stream of benzene 54 are fed into an alkylation unit 56. The alkylation unit 56 holds a catalyst 58, such as a solid acid catalyst, that supports alkylation of the benzene 54 with the mono-olefins 52. Hydrogen fluoride (HF) and aluminum chloride ($AlCl_3$) are two major catalysts in commercial use for the alkylation of benzene with linear mono-olefins and may be used in the alkylation unit 56. Additional catalysts include zeolite-based or fluoridate silica alumina-based solid bed alkylation catalysts (for example, FAU, MOR, UZM-8, Y, X RE exchanged Y, RE exchanged X, amorphous silica-alumina, and mixtures thereof, and others known in the art). As a result of alkylation, alkylbenzene, typically called linear alkylbenzene (LAB), is formed according to the reaction:

$$C_6H_6 + C_XH_{2X} \rightarrow C_6H_5C_XH_{2X+1}$$

and are present in an alkylation effluent 60.

To optimize the alkylation process, surplus amounts of benzene 54 are supplied to the alkylation unit 56. Therefore, the alkylation effluent 60 exiting the alkylation unit 56 contains alkylbenzene and unreacted benzene. Further, the alkylation effluent 60 may also include some unreacted paraffins. In FIG. 2, the alkylation effluent 60 is passed to a benzene separation unit 62, such as a fractionation column, for separating the unreacted benzene from the alkylation effluent 60. This unreacted benzene exits the benzene separation unit 62 in a benzene recycle stream 64 that is delivered back into the alkylation unit 56 to reduce the volume of fresh benzene needed in stream 54.

As shown, a benzene-stripped stream 66 exits the benzene separation unit 62 and enters a paraffinic separation unit 68, such as a fractionation column. In the paraffinic separation unit 68, unreacted paraffins are removed from the benzene-stripped stream 66 in a recycle paraffin stream 70, and can be routed to and mixed with the first portion of paraffins 24 before dehydrogenation as described above, or can optionally be directed to the second portion 26 for purification of product paraffins.

Further, an alkylbenzene stream 72 is separated by the paraffinic separation unit 68 and is fed to an alkylate separation unit 74. The alkylate separation unit 74, which may be, for example, a multi-column fractionation system, separates a heavy alkylate bottoms stream 76 from the alkylbenzene stream 72.

As a result of the post-alkylation separation processes, the linear alkylbenzene product 12 is isolated and exits the subsystem 10. It is noted that such separation processes are not necessary in all embodiments in order to isolate the alkylbenzene product 12. For instance, the alkylbenzene product 12 may be desired to have a wide range of carbon chain lengths and not require any fractionation to eliminate carbon chains longer than desired, i.e., heavies or carbon chains shorter than desired, i.e., lights. Further, the feed 114 may be of sufficient quality that no fractionation is necessary for the desired chain length range.

In FIG. 2, to produce linear olefins, a stream 53, which may include all or a portion of stream 52, is directed to a separator 57 for separating the unconverted paraffins from the olefins. In one particular embodiment, the separator 57 is an Olex® separator, available from UOP LLC. The Olex® process involves the selective adsorption of a desired component (i.e., olefins) from a liquid-phase mixture by continuous contacting with a fixed bed of adsorbent. In another particular embodiment, the separator 57 is a direct sulfonation separator. The separated, unconverted paraffins may optionally be directed back to the second paraffin portion 26 for purification (stream 73) and/or back to the first paraffin portion 24 for dehydrogenation for conversion to olefins (stream 71).

In FIG. 2, an olefins stream 61 exits the separator 57 and is fed to a separator 63. The separator 63 may be a multi-stage fractionation unit, distillation system, or similar known apparatus. The separator 63 may provide a means to separate the olefins into various desirable fractions. For example, as shown in FIG. 2, a first portion of olefins 65 and a second portion of olefins 65 are illustrated, although any number of olefin portions may be provided, depending on how many olefin fractions are desired. In certain embodiments, the first portion of olefins 65 has carbon chain lengths of $C_{10}$ to $C_{14}$. In other embodiments, the first portion of olefins 65 has carbon chain lengths having a lower limit of $C_L$, where L is an integer from four (4) to thirty-one (31), and an upper limit of $C_U$, where U is an integer from five (5) to thirty-two (32). The second portion of olefins 67 may have carbon chains shorter than, longer than, or a combination of shorter and longer than, the chains of the first portion of olefins 65. In one particular embodiment, the first portion of olefins 65 includes olefins with $C_{10}$ to $C_{14}$ chains and the second portion of olefins 67 includes olefins with $C_{18}$ to $C_{20}$ chains. Subsequent to separation, the purified olefins portions 65 and 67 are removed from the subsystem 10 as the olefin product.

With reference now to exemplary natural oil feeds 114 of FIG. 1 that may be supplied to system 100, in addition to the kerosene feed 102, in certain embodiments, the feed 114 is substantially homogeneous and includes free fatty acids within a desired range. For instance, the feed may be palm fatty acid distillate (PFAD). Alternatively, the feed 114 may include triglycerides and free fatty acids that all have carbon chain lengths appropriate for a desired linear alkylbenzene product 12, linear paraffin product 13, or linear olefin products 65, 67.

In certain embodiments, the natural oil source is castor, and the feed 114 includes castor oils. Castor oils consist essentially of $C_{18}$ fatty acids with additional, internal hydroxyl groups at the carbon-12 position. For instance, the structure of a castor oil triglyceride is:

During deoxygenation of a feed 114 comprising castor oil, it has been found that some portion of the carbon chains are cleaved at the carbon-12 position. Thus, deoxygenation creates a group of lighter paraffins having $C_{10}$ to $C_{11}$ chains resulting from cleavage during deoxygenation, and a group of non-cleaved heavier paraffins having $C_{17}$ to $C_{18}$ chains. With reference again to subsystem 10 in FIG. 2, the lighter paraffins may form the first portion of paraffins 24 and the heavier paraffins may form the second portion of paraffins 26. It should be noted that while castor oil is shown as an example of an oil with an additional internal hydroxyl group, others may exist. Also, it may be desirable to engineer genetically modified organisms to produce such oils by design. As such, any oil with an internal hydroxyl group may be a desirable feed oil.

Figure 3:
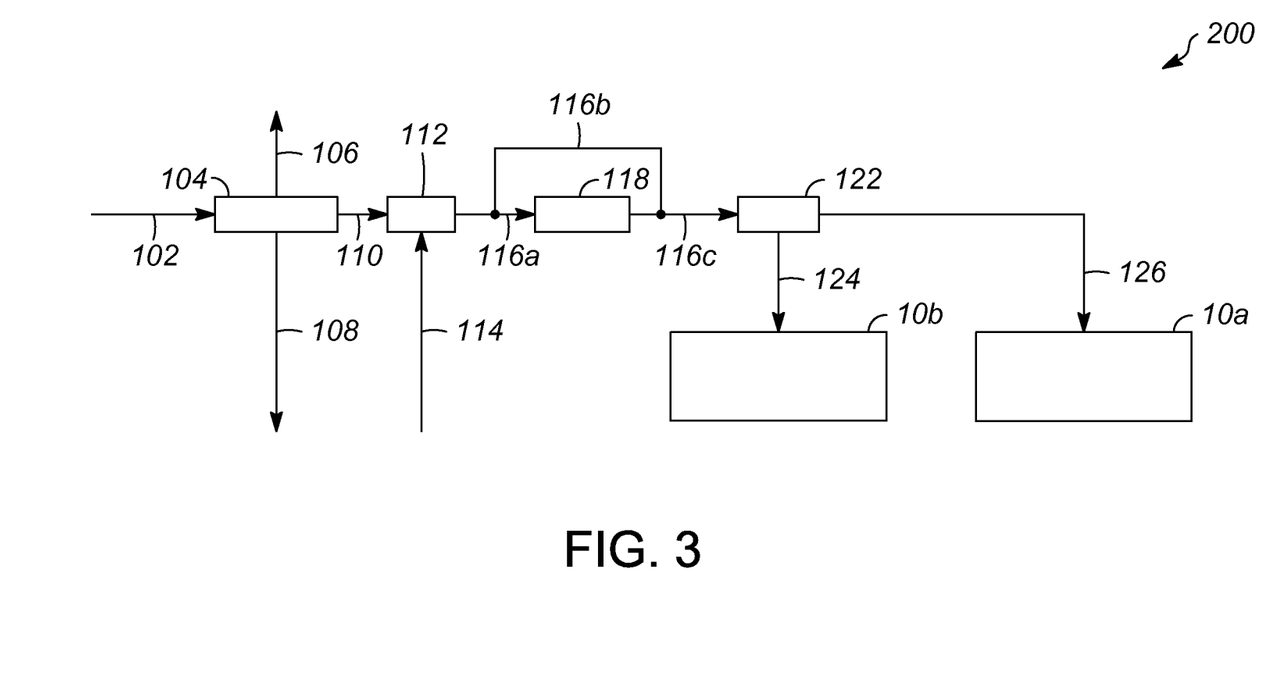
FIG. 3 schematically illustrates another exemplary embodiments of a system utilizing a process for producing linear alkylbenzenes, paraffins, and/or olefins from natural oils and kerosene.

FIG. 3 depicts a system 200 using another exemplary embodiment of a process for producing a linear alkylbenzene, paraffin, or olefin from natural oil and kerosene. In this embodiment, the heavy paraffins stream 124 is not directed out of the system 200 for optional use in other processes as in FIG. 1, but rather is directed to a second subsystem 10b (stream 126 being directed to a first subsystem 10a) for the production of linear alkylbenzenes, paraffins, and/or olefins that are heavier than the heart cut. Subsystems 10a and 10b operate in the same manner as described above with regard to subsystem 10. In one example, subsystems 10a and 10b are separate systems for the simultaneous processing of the heart cut and the heavier paraffins, respectively. In other examples, subsystems 10a and 10b are the same system, wherein the heart cut and heavier paraffins are processed at different times.

Figure 4:
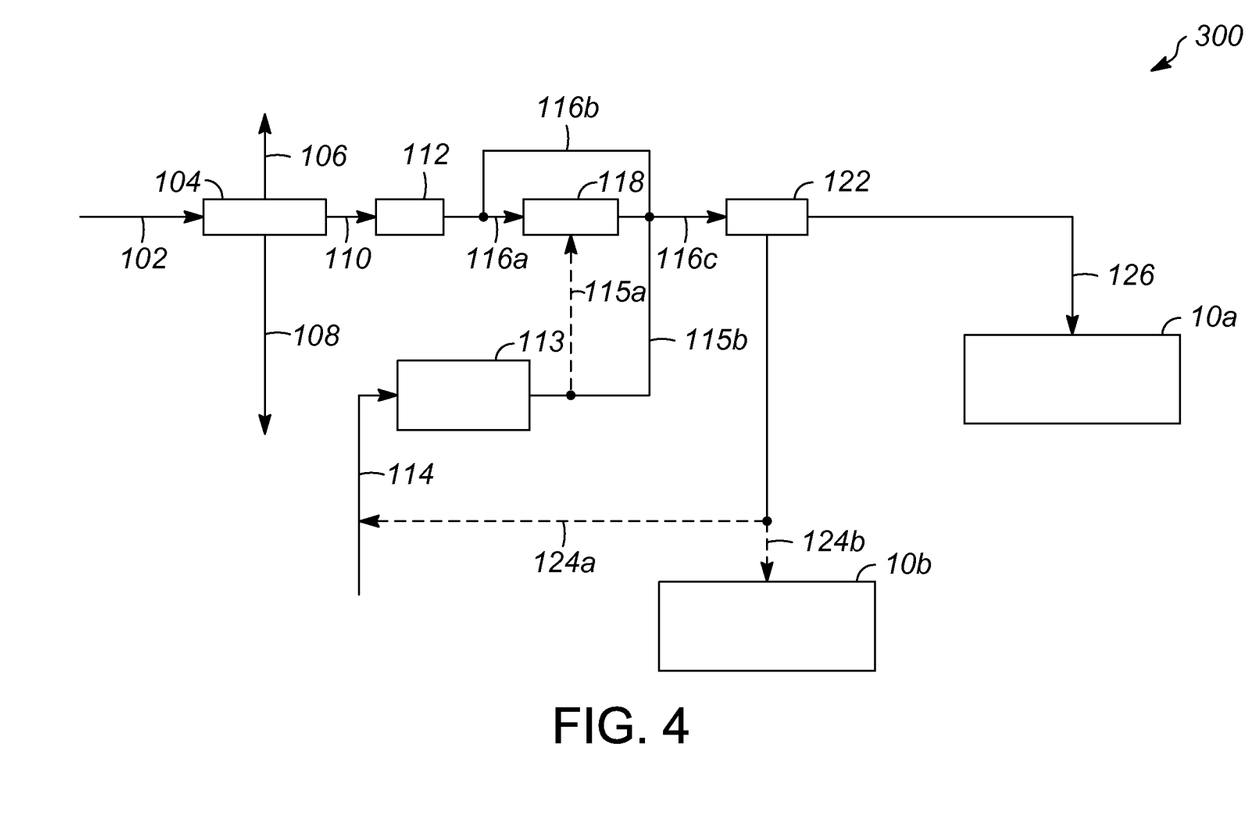
FIG. 4 schematically illustrates another exemplary embodiment of a system utilizing a process for producing linear alkylbenzenes, paraffins, and/or olefins from natural oils and kerosene.

FIG. 4 depicts a system 300 using yet another exemplary embodiment of a process for producing a linear alkylbenzene, paraffin, or olefin from natural oil and kerosene. In this embodiment, the natural oil feed stream 114 is deoxygenated into paraffins in a deoxygenation apparatus 113 prior to being combined with the paraffins from the kerosene feed 102. As such, the KHT 112 does not need to be configured for deoxygenation, and a catalyst used therein can be selected solely for denitrification and desulfurization purposes. In one example, a stream 115a of paraffins exits the deoxygenation apparatus 113 and is fed to the separator 118 where separation of branched and aromatic compounds is required. In an alternative example, a stream 115b of paraffins is combined with the kerosene paraffins downstream of the separator 118, where such separation is not required. In this embodiment, the heavy paraffins may either be removed from system 300 as discussed above with regard to FIG. 1 (stream 124a), or further processed into linear alkylbenzenes, paraffins, and/or olefins as discussed above with regard to FIG. 3.

Figure 5:
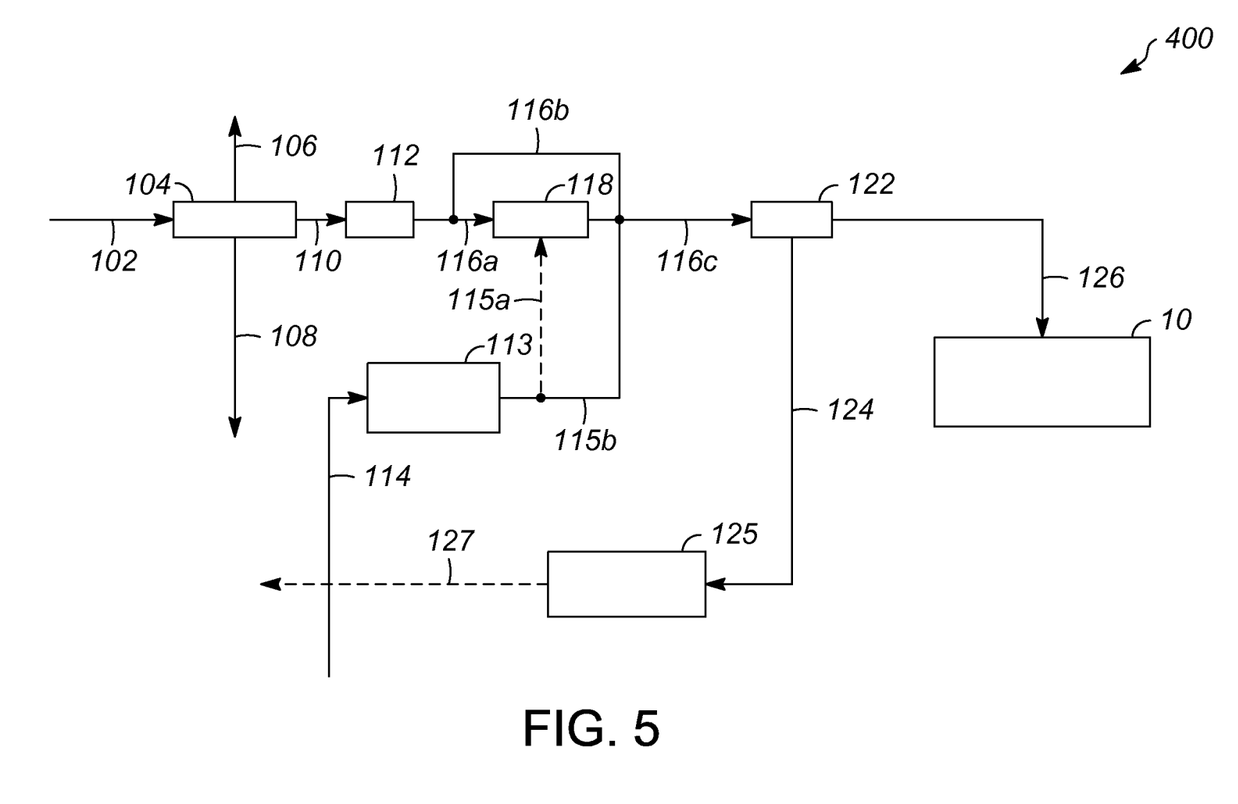
FIG. 5 schematically illustrates yet another exemplary embodiment of a system utilizing a process for producing linear alkylbenzenes, paraffins, and/or olefins from natural oils and kerosene.

FIG. 5 depicts a system 400 using still another exemplary embodiment of a process for producing a linear alkylbenzene, paraffin, or olefin from natural oil and kerosene. In this embodiment, heavy paraffins stream 124 is directed to an isomerization reactor 125. The isomerization reactor 125 is provided to convert the heavy linear paraffins stream 124 into a steam of branched paraffins and other compounds 127, which have other industrial uses such as fuel.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for producing a linear paraffin product from natural oil and kerosene comprising:
    providing a first feed stream comprising kerosene;
    pre-fractionating the first feed stream to produce a heart cut paraffin stream comprising paraffins in a heart cut range;
    combining the heart cut paraffin stream with a second feed stream comprising natural oil to form a combined stream;
    deoxygenating the natural oil to form paraffins, wherein the deoxygenating comprises catalytically deoxygenating the natural oil prior to, at the same time as, or after combining the heart cut paraffin stream with the second feed stream;
    fractionating the combined stream to remove paraffins that are heavier than the heart cut range;
    separating linear paraffins from branched or cyclic compounds in the combined stream; and
    denitrifying and desulfurizing the heart cut paraffin stream.

2. The method of claim 1, wherein pre-fractionating the first feed stream to produce the heart cut paraffin stream comprises pre-fractionating the first feed stream to produce a $C_{10}$-$C_{13}$ paraffin stream.

3. The method of claim 1, further comprising separating one or more of branched hydrocarbons and cyclic hydrocarbons from the combined stream.

* * * * *